United States Patent [19]

Takahata et al.

[11] Patent Number: 4,731,226

[45] Date of Patent: Mar. 15, 1988

[54] GAS SENSOR

[75] Inventors: Kei Takahata, Yokkaichi; Yoshinobu Matsuura, Toyonaka, both of Japan

[73] Assignee: Figaro Engineering Inc.

[21] Appl. No.: 875,470

[22] Filed: Jun. 18, 1986

[30] Foreign Application Priority Data

Jun. 24, 1985 [JP] Japan .................................. 60-138811

[51] Int. Cl.$^4$ ........................................... G01N 27/12
[52] U.S. Cl. .................................... 422/98; 73/27 R; 338/34; 422/94
[58] Field of Search ...................... 73/23.27 R; 338/34; 422/94-98; 436/132, 139, 141, 144, 152

[56] References Cited

U.S. PATENT DOCUMENTS 4,013,943  3/1977  Chou et al. ...................... 73/27 R X
4,033,169  7/1977  Fujishiro et al. ........................ 73/23

FOREIGN PATENT DOCUMENTS 0157328  9/1985  European Pat. Off. .
53-96894  8/1978  Japan ..................................... 73/23
54-104397 8/1979  Japan ..................................... 422/98
54-104392 8/1979  Japan ..................................... 422/98
55-78235  6/1980  Japan ..................................... 338/34
60-100752 6/1985  Japan .

OTHER PUBLICATIONS

Patent Abstracts of Japan, vol. 9, No. 250, (P-394), [1973], 10/8/85; & JP-A-60 100 752, JP-A-60 100 753, JP-A-60 100 754, (Fuigaro Giken K.K.), 4/6/85.
Electronic Engineering, vol. 57, No. 701, May 1985, pp. 47-57; J. Watson et al.; "A Solid-State Gas Sensor".

Primary Examiner—Barry S. Richman
Assistant Examiner—Michael S. Gzybowski
Attorney, Agent, or Firm—Kane, Dalsimer, Kane, Sullivan and Kurucz

[57] ABSTRACT

A gas sensor in which a compound of rhenium is added to tin oxide ($SnO_2$). Rhenium inhibits the sensor from lowering its resistance over time and in particular increases its durability against overheating. Rhenium is preferably used together with vanadium. Rhenium is preferably added by impregnation in order to maintain temperature characteristic of the sensor.

6 Claims, 11 Drawing Figures

GAS SENSOR

BACKGROUND OF THE INVENTION

1. Field of the Invention

The present invention relates to gas sensors which make use of the change in resistance of tin oxide ($SnO_2$), and more particularly relates to stabilizing the gas sensors resistance over time. The gas sensor according to the present invention is suitable for detection of combustible gases such as methane and butane, and poisonous gases such as carbon monoxide.

2. Brief Description of the Prior Art

Generally gas sensors are made of metallic oxide semiconductors and their resistance value gradually lowers with use. As a result the gas sensors sensitivity to detect gas changes with time.

Japanese patent laid open No. 60-100, 752 discloses the addition of vanadium pentoxide ($V_2O_5$) to gas sensors made of $SnO_2$ to effectively inhibit this change in resistance with time. However, the addition of $V_2O_5$ alone does not sufficiently improve the sensors thermal resistance.

The applicant has therefore screened different materials, mainly transition metal oxides, searching for a suitable substitute for $V_2O_5$ and has found that only rhenium (Re) satisfies this need.

SUMMARY OF THE INVENTION

Accordingly, the object of the invention is to provide a gas sensor containing $SnO_2$ that does not lower its resistance with time.

The invention inhibits a gas sensor from lowering its resistance when it is continuously overheated at high temperatures over long periods of time.

The gas sensor according to the invention is characterized by adding rhenium to a gas sensitive element having $SnO_2$ as an available component. Rhenium is effective in preventing the sensor from lowering its resistance, and in particular improves the sensors durability against high temperatures.

Rhenium exhibits its influence when it is added to the gas sensing element as a uniform addition. If the gas sensitive element employing $SnO_2$ is already a sintered compact, rhenium can be added only to the surface of the sensitive element. When a thermal resistant insulating material such as aggregate of alumina is added to the gas sensitive element, rhenium can be added to the thermal resistant insulating material instead of to the $SnO_2$. At present the reasons why rhenium is so effective even when it is not added uniformly to $SnO_2$ or to the aggregate of alumina, are not always clear. When adding rhenium uniformly to $SnO_2$, a preferable quantity is from about 1 to about 150 mg of $Re_2O_7$ per gram of $SnO_2$. A more preferable range is from about in the range of 4 to about 80 mg of $Re_2O_7$.

Rhenium is added in the form of either a simple substance or a compound such as a metal oxide. Existing conditions of rhenium are variable and indefinite depending on the atmosphere to which a sensor is exposed. The most stable rhenium compounds are $Re_2O_7$ and $ReO_2$.

The excellent effect of rhenium can be exhibited when it is used together with a simple substance of palladium (Pd), platinum (Pt), iridium (Ir), ruthenium (Ru), osmium (Os), rhodium (Rh), etc. or a compound of noble metal oxide thereof, otherwise with compounds of transition metal oxides of iron (Fe), nickel (Ni), chromium (Cr), cobalt (Co), vanadium (V), wolfram (W), molybdenum (Mo), etc. This means that rhenium is adapted to complex action with materials of high oxidation activity. It has been found that vanadium is the most preferable material for such complex action.

Rhenium is particularly effective when applied to a system using a silica binder, such as ethyl silicate or silica gel.

Any gas sensitive element can be used as long as its main component is $SnO_2$. Other metal oxide semi-conductors, noble metals, etc., can be further added to the gas sensitive element within a range not affecting the superiority of $SnO_2$.

Terminology:

In the present specification, the term "1 wt. %" means an addition of 10 mg per 1 g of $SnO_2$, and the quantity of rhenium addition is expressed in terms of $Re_2O_7$. In principle, the addition is described in the form of the quantity added to the total quantity of $SnO_2$ present, even for non-uniform additions to the $SnO_2$.

The term "self-heating gas sensor" (or exothermic gas sensor) means a sensor which heats itself solely from the heat generated due to the detecting current supplied to the sensor or in combination with the power for the heater. The self-heating gas sensor is usually heated by both the power for heater and self-heating generation, in a reducing gas atmosphere. The temperature rises when the detecting current is increased. In such a self-heating gas sensor, the maximum temperature is higher than the clean air by at least 50° C., and generally higher than clean air by no less than 180° C. The self-heating gas sensor is characterized by its sensitivity to aging when it is put in the gas because of rise in temperature due to the gas. The gas sensor is also characterized by its high dependence on the heating temperature since its operating temperature is different depending on whether the gas sensor is put in the gas or clean air.

Other objects and features of the present invention will become apparent in the course of the following description together with the accompanying drawings and tables.

BRIEF DESCRIPTION OF THE DRAWINGS

In the drawings forming a part of the present application.

DESCRIPTION OF THE PREFERRED EMBODIMENT

Gas Sensor

An aqueous solution of stannic chloride (Sn Cl$_4$) is hydrolyzed by ammonia (NH$_3$) to obtain a sol of stannic acid. The ammonium ion and the chlorine ion are eliminated by centrifuging after adding water to the sol. It is then baked at 800° C. for one hour in air; after air drying, SnO$_2$ is obtained. Alternatively one can start with SnO$_2$ and the baking condition can be varied within the range of 500° to 900° C.

The SnO$_2$ is impregnated with a solution of aqua regia of Pd, and pyrolyzed at 600° C. for 30 minutes in air for supporting the Pd. Since Pd exists mainly in the form of PdO, the addition is hereinafter expressed in terms of PdO. Pd is added for improving the response of the sensor and its relative sensitivity to the various gases, and therefore it is not always necessary to add it. Further, Pd can be substituted with noble metal such as Pt, Rh, Ir or transition metal oxides such as manganese oxide (Mn$_2$OP$_3$) and ferric oxide (Fe$_2$O$_3$). Rhenium exhibits its effect in combination with these metals.

In the case of adding aggregate 1000 mesh alpha alumina ($\alpha$-Al$_2$O$_3$), the aggregate is mixed at equal weight with SnO$_2$ to make the gas sensitive material. When no aggregate is added, SnO$_2$ is used as the gas sensitive material after adding Pd thereto. Unless otherwise described herein, aggregate is not added in the described embodiment.

Figure 1:
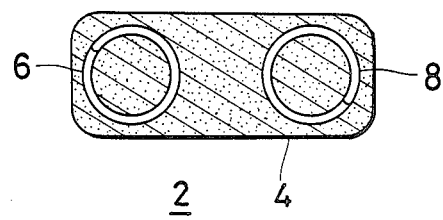
FIGS. 1 and 2 are sectional views of the gas sensors embodied in the invention.
Figure 2:
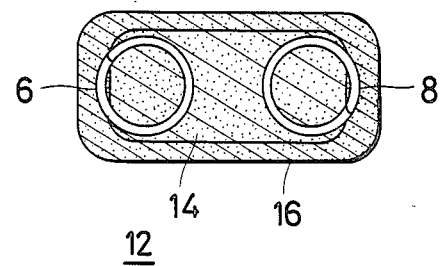
Figure 3:
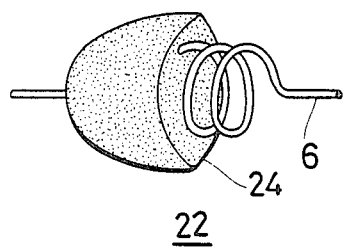
FIG. 3 is a partially cutaway view of a gas sensor as a modification.

The gas sensitive material is molded into compacts as shown in FIGS. 1 to 3 and sintered at 800° C. for 10 minutes. Silica binder is added to the compact before sintering, if necessary. The binder is composed of ethyl silicate or silica sol (material free from alkali metal ions). These binder materials are converted to silica during sintering and improve the strength of the sensor. The quantity of binder added is expressed in terms of SiO$_2$. The addition of rhenium is particularly advantageous in a system containing binders.

Addition of rhenium

The most preferable embodiment of the invention is attained when rhenium and vanadium are added together. Rhenium and vanadium are normally added simultaneously, but can be added one after the other. Vanadium exists mainly in the form of V$_2$O$_5$ in the sensor, and therefore the quantity of the vanadium addition is hereinafter expressed in terms of V$_2$O$_5$. As a matter of course, rhenium can be added alone without vanadium. Further, rhenium and vanadium can be added in the form of either an aqua regia solution thereof or a chloride solution thereof.

For a uniform addition of rhenium to the SnO$_2$, rhenium is added simultaneously with the Pd, but they can be added sequentially. Furthermore, when adding rhenium to the aggregate, the aggregate is impregnated with a solution of rhenium and pyrolyzed at 600° C. for 30 minutes after air drying, then rhenium is added. For non-uniform additions to the gas sensitive element, after sintering the sensitive element is impregnated with a solution of rhenium and pyrolyzed at 600° C. for 30 minutes. In this case, rhenium segregates on the surface of the sensitive element, and does not remain inside the sensitive element. In the process of pyrolysis, rhenium is converted to ReO$_2$, Re$_2$O$_7$, etc., while vanadium is mainly converted to V$_2$O$_5$.

Construction of sensor

FIG. 1 shows a sensor to which rhenium is uniformly added, and wherein (4) denotes the gas sensitive element mainly composed of SnO$_2$ and (6), (8) denote a pair of electrodes which also serve as heaters.

FIG. 2 shows a sensor (12) with rhenium segregated on the surface, and wherein (14) denotes the gas sensitive element, (16) denotes a segregation layer, and (6), (8) are electrodes which also serve as heaters. The quantity of SnO$_2$ in this sensor is 15 mg, and this is used as a reference to express the quantity of the addition of rhenium and other chemicals.

FIG. 3 shows a sensor (22) with a single electrode (6) alone which also serves as a heater, and wherein (24) denotes the gas sensitive element. In this sensor, when changing the resistance value of the sensitive element (24), the parallel resistance value between the electrode (6) and the sensitive element (24) is changed, and this change is used as the output.

Construction of the sensor is not limited to those described above, and any other known constructions can be used.

Measurement

Tables 1 to 11 show the characteristics with respect to the several basic embodiments of the invention. Unless otherwise specified herein every sensor has 0.8 wt. % of PdO is added to the SnO$_2$ and is impregnated with rhenium and/or vanadium. Neither an aggregate of alumina nor silica binder is added in principle. The same number in the tables means the same lot of sensor. A number without suffix means that the sensor is used in self-heating conditions. Suffix (s) means that the sensor is used under a constant temperature of 400° C. The basic samples include a Sample (1) as a comparative example in which neither rhenium nor vanadium is added, Sample (2) in which 2.4 wt. % of rhenium in terms of Re$_2$O$_7$ is added, and Sample (3) in which 2.4 wt. % of rhenium and 0.42 wt. % of vanadium in terms of V$_2$O$_5$ (quantity of vanadium is hereinafter expressed in terms of V$_2$O$_5$) are added.

Measurement is carried out in clean air and in gases of 3500 ppm each, and the atmosphere is 20° C. and 65% in relative humidity. Result is expressed in an average value of five sensors. In addition, the sensors are heated for two weeks under service conditions before starting measurement to eliminate any possible influence from being newly manufactured.

Figure 4:
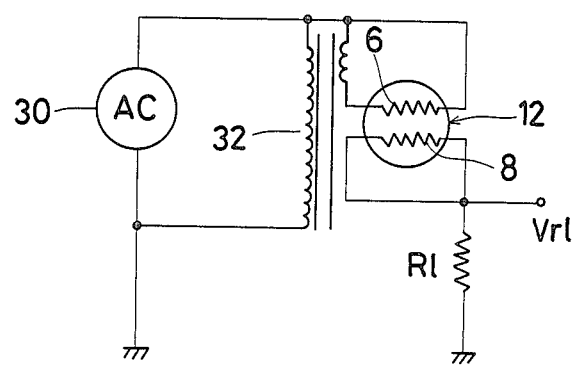
FIG. 4 is a circuit diagram of a circuit incorporated in a self-heating gas sensor.

The circuit shown in FIG. 4 is applied to the sensors in principle, and the sensors are used under self-heating conditions. In FIG. 4, numeral (30) denotes an alternating current source of 100 V, (32) denotes a transformer, and (R1) denotes a load resistance of approximately 3.5 K$\Omega$. In the drawing, the sensor (12) is heated by power supplied to the electrode (6) which also serves as a heater and by self-heat generation due to the detection current. Since the resistance of the sensor is high in the air, the self-heat generation can be ignored and the temperature of the sensor is 300° to 320° C., while the resistance value of the sensor is low in gases, and the temperature of the sensor is raised to no less than 500° C. The change in the resistance value of the sensor is measured from voltage (Vrl) applied to the load resistance (R1).

Figure 5:
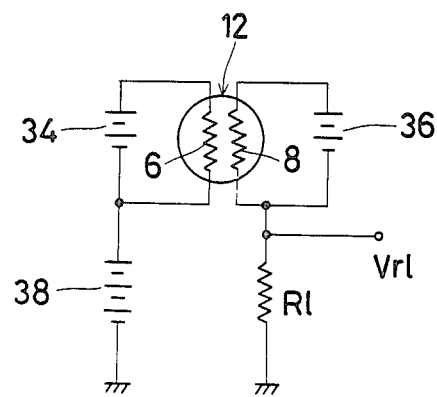
FIG. 5 is a circuit diagram of a circuit used in measurement.

FIG. 5 shows the circuit when the sensor temperature is constantly at 400° C. Power sources (34), (36) are connected to two electrodes (6), (8) which also serve as heaters, and detection current is applied from a detection power source (38). The output of the power source (38) is so small that self-heat generation thereby can be ignored. In addition, the effects exhibited by rhenium and vanadium remain unchanged even when changing their heating conditions, irrespective of heating at a constant temperature of self-heat generation.

The following are tables with respect to isobutane ($C_4H_{10}$) which is a representative constituent of LPG (liquefied petroleum gas), i.e., Table 1 shows an influence when a sensor is left unused, Table 2 shows the influence when the sensor is used intermittently, and Table 3 shows the influence when the sensor is used continuously. As seen in Table 3, the control sensor (Sample No. 1) has a problem with its reliability over time when it is used continuously. Such transitory deterioration is improved by the addition of rhenium alone (Sample No. 2) or together with vanadium (Sample No. 3), irrespective of self-heat generation or heating at constant temperature. In addition, the tables from Tables 4 onward show characteristics in the case of continuous use.

TABLE 1

(Influence when a sensor is left unused)*
Sensor resistance (Rs) (KΩ) (in $C_4H_{10}$3500 ppm)

| Sample No. | Additive | (wt %) | Initial value | 50 days later | 100 days later | 200 days later |
|---|---|---|---|---|---|---|
| 1 | — | | 2.0 | 2.2 | 2.3 | 2.2 |
| 2 | $Re_2O_7$ | 2.4 | 1.5 | 1.6 | 1.5 | 1.5 |
| 3 | $Re_2O_7$ $V_2O_5$ | 2.4 0.42 | 1.6 | 1.6 | 1.6 | 1.6 |

*$C_4H_{10}$ denotes isobutane

TABLE 2

(Influence when a sensor is intermittently used)*
Sensor resistance (Rs) (KΩ) (in $C_4H_{10}$3500 ppm)

| Sample No. | Additive | (wt %) | Initial value | 50 days later | 100 days later | 200 days later |
|---|---|---|---|---|---|---|
| 1 | — | | 2.0 | 2.3 | 2.4 | 2.2 |
| 2 | $Re_2O_7$ | 2.4 | 1.6 | 1.6 | 1.7 | 1.5 |
| 3 | $Re_2O_7$ $V_2O_5$ | 2.4 0.42 | 1.6 | 1.6 | 1.6 | 1.6 |

*Repetition of 5 days use and another 5 days of non-use.

TABLE 3

(Influence when a sensor is continuously used)
Sensor resistance (RS) (K) (in $C_4H_{10}$3500 ppm)

| Sample No. | Additive | (wt %) | Initial value | 50 days later | 100 days later | 200 days later |
|---|---|---|---|---|---|---|
| 1 | — | | 2.1 | 1.7 | 1.5 | 1.2 |
| 2 | $Re_2O_7$ | 2.4 | 1.6 | 1.5 | 1.5 | 1.5 |
| 3 | $Re_2O_7$ $V_2O_5$ | 2.4 0.42 | 1.6 | 1.6 | 1.6 | 1.6 |
| 1s | — | | 1.6 | 1.3 | 1.2 | 1.0 |
| 2s | $Re_2O_7$ | 2.4 | 1.5 | 1.5 | 1.5 | 1.4 |
| 3s | $Re_2O_7$ $V_2O_5$ | 2.4 0.42 | 1.7 | 1.6 | 1.6 | 1.6 |

Table 4 shows the result when the quantity of the rhenium addition is changed. There is no limit in the quantity of the addition in principle, but it is preferable to add 0.4 to 8 wt. % of rhenium, or more extensively 0.1 to 15 wt. %. Within the range of such addition, superior durability can be attained against high temperature due to overheating or the complex acceleration described later.

TABLE 4

(Addition of $Re_2O_7$)
Sensor resistance (Rs) (K) (in $C_4H_{10}$3500 ppm)

| Sample No. | $Re_2O_7$ (wt %) | Initial value | 50 days later | 100 days later | 200 days later |
|---|---|---|---|---|---|
| 1 | — | 2.1 | 1.7 | 1.5 | 1.2 |
| 4 | 0.64 | 1.9 | 1.9 | 1.8 | 1.7 |
| 5 | 1.6 | 1.7 | 1.7 | 1.7 | 1.6 |
| 2 | 2.4 | 1.6 | 1.5 | 1.5 | 1.5 |
| 6 | 4.0 | 1.8 | 1.7 | 1.8 | 1.7 |

The effect attained by addition of rhenium is not limited to only the detection of isobutane. Table 5 shows the ratio of the resistance value at 200 days the the initial resistance value for various gases.

TABLE 5

(Behavior on other gases)
Ratio between resistance values ($R_{200}/R_0$)

| Sample No | Additive | (wt %) | $CH_4$ | $H_2$ | CO | EtOH* | Air |
|---|---|---|---|---|---|---|---|
| 1 | — | | 0.7 | 0.5 | 0.8 | 0.5 | 0.7 |
| 2 | $Re_2O_7$ | 2.4 | 1.0 | 0.8 | 1.0 | 0.8 | 1.0 |
| 3 | $Re_2O_7$ $V_2O_5$ | 2.4 | 1.0 | 1.0 | 1.0 | 0.9 | 1.0 |

*denotes ethanol.

The effect of rhenium is greater when using a silica binder. Table 6 shows the effects of using ethyl silicate (3 wt. % addition of silica to the $SnO_2$) and silica sol (4 wt. % addition of silica to the $SnO_2$).

TABLE 6

(Complex action with silica)
Ratio between resistance values ($R_{200}/R_0$)

| Sample No. | Silica (wt %) | Rhenium | (wt %) | $C_4H_{10}$ | $CH_4$ | $H_2$ |
|---|---|---|---|---|---|---|
| 11 | 3 (Ethyl silicate) | — | | 0.5 | 0.6 | 0.5 |
| 12 | " | $Re_2O_7$ | 2.4 | 1.0 | 1.0 | 0.9 |
| 13 | " | $Re_2O_7$ $V_2O_5$ | 2.4 0.42 | 1.0 | 1.0 | 1.0 |
| 21 | 4 (Silica sol) | — | | 0.6 | 0.7 | 0.6 |
| 22 | " | $Re_2O_5$ | 2.4 | 1.0 | 1.0 | 0.9 |
| 23 | " | $Re_2O_7$ $V_2O_5$ | 2.4 0.42 | 1.0 | 1.0 | 1.0 |

Table 7 shows results when rhenium is added by other methods.

TABLE 7

(Other methods of addition)
Ratio between resistance values ($R_{200}/R_0$)

| Sample No. | Rhenium | (wt %) | $C_4H_{10}$ | $CH_4$ | $H_2$ |
|---|---|---|---|---|---|
| 1 | — | | 0.6 | 0.7 | 0.5 |
| 32 | $Re_2O_7$ mixed uniformly with $SnO_2$ | 2.4 | 0.9 | 1.0 | 0.8 |
| 33 | $Re_2O_7$ $V_2O_5$ both added uniformly to $S_nO_2$ | 2.4 0.24 | 1.0 | 1.0 | 1.0 |
| 41 | alumina aggregate added | — | 0.6 | 0.8 | 0.5 |
| 42 | $Re_2O_7$ added to alumina aggregate | 1.0 | 0.9 | 1.0 | 0.8 |

Table 8 shows a partial comparison of the inventor's results when the sensitive element is impregnated with materials other than rhenium. It is found that desired effect is attained only when adding vanadium.

TABLE 8

(Comparative examples)
Ratio between resistance value ($R_{200}/R_0$)

| Sample No. | Additive | (wt %) | $C_4H_{10}$ | $H_2$ |
|---|---|---|---|---|
| 1 | — | | 0.6 | 0.5 |
| 51 | $Rh_2O_3$ | 2 | 0.5 | 0.6 |
| 52 | $Mn_2O_3$ | 2 | 1.5 | 0.8 |
| 53 | $Fe_2O_3$ | 2 | 1.6 | 0.6 |
| 54 | $MoO_3$ | 2 | 1.4 | 0.5 |
| 55 | $V_2O_5$ | 0.42 | 0.9 | 0.8 |

Figure 6:
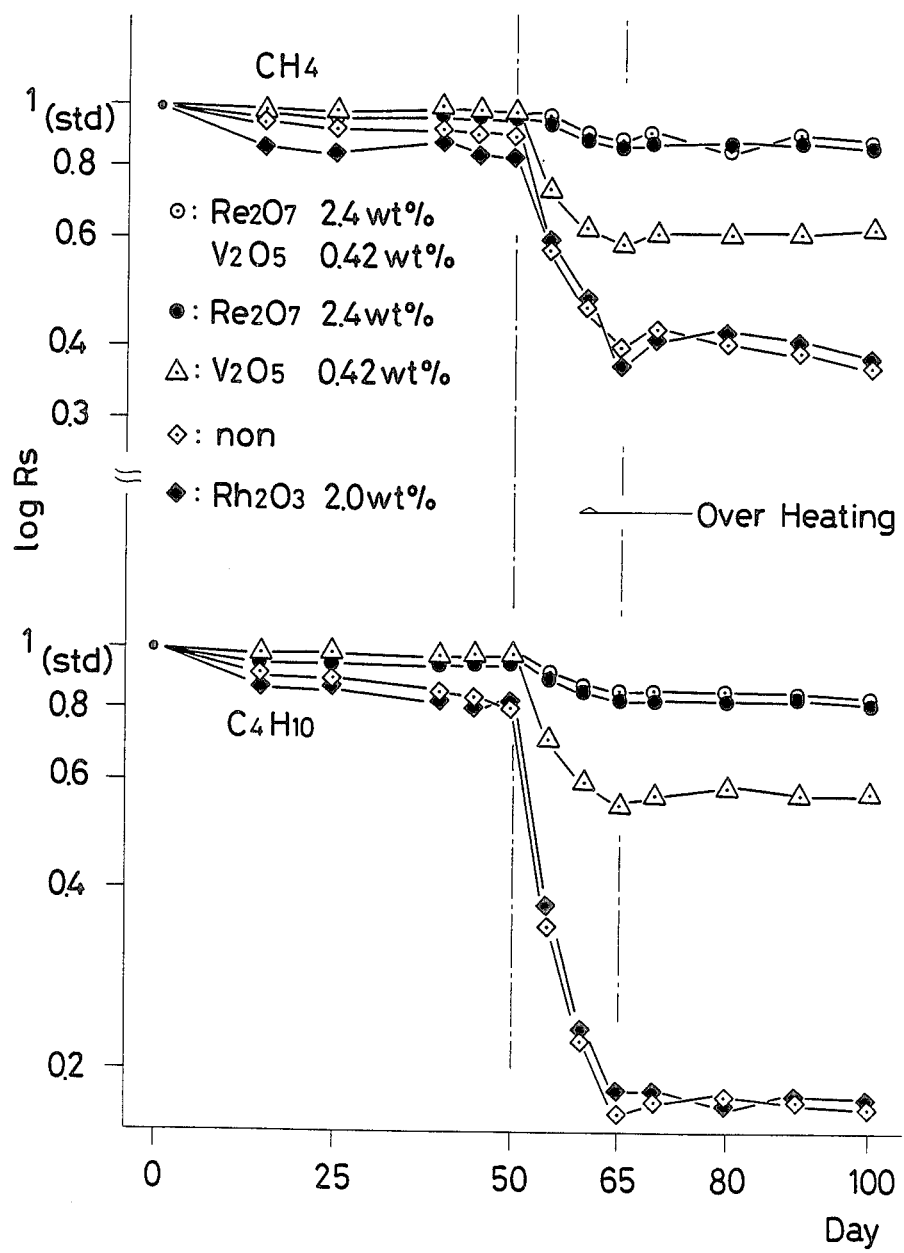
FIG. 6 shows the characteristics of a sensor with respect to high temperature due to overheating.

Table 9 and FIG. 6 show the results of overheating a sensor continuously. After using it for 50 days under self-heating service conditions, the sensor is heated at 550° C. for 15 days by using two electrodes (6), (8) as heaters. After heating, the sensor is returned to the self-heating service conditions. This test examines the thermal resistance of the sensor as well as its durability when it is overheated due to abnormal treatment. FIG. 6 shows the results establishing a resistance value in gases (3500 ppm) using the starting valves as the reference. On the other hand, Table 9 shows results establishing a resistance value in gases using the values before overheating as a reference. Durability against overheating is improved by addition of of $V_2O_5$ but it is still not sufficient. Thermal resistance is not improved when the sensor is impregnated with 2 wt. % of $Rh_2O_3$ as shown in FIG. 6. High durability is insured by addition of rhenium. The results shown herein are obtained by the method in which the rhenium is segregated on the surface of the sensitive element, but almost the same results are obtained when it is added uniformly to $SnO_2$.

TABLE 9

(The overheating test)
Ratio between resistance values (before/after testing)

| Sample No. | Additive | (wt %) | $C_4H_{10}$ | $CH_4$ |
|---|---|---|---|---|
| 1 | — | | 0.2 | 0.5 |
| 55 | $V_2O_5$ | 0.42 | 0.6 | 0.6 |
| 4 | $Re_2O_7$ | 0.64 | 0.9 | 0.9 |
| 2 | $Re_2O_7$ | 2.4 | 0.9 | 0.9 |
| 6 | $Re_2O_7$ | 4.0 | 0.9 | 0.9 |

Figure 7:
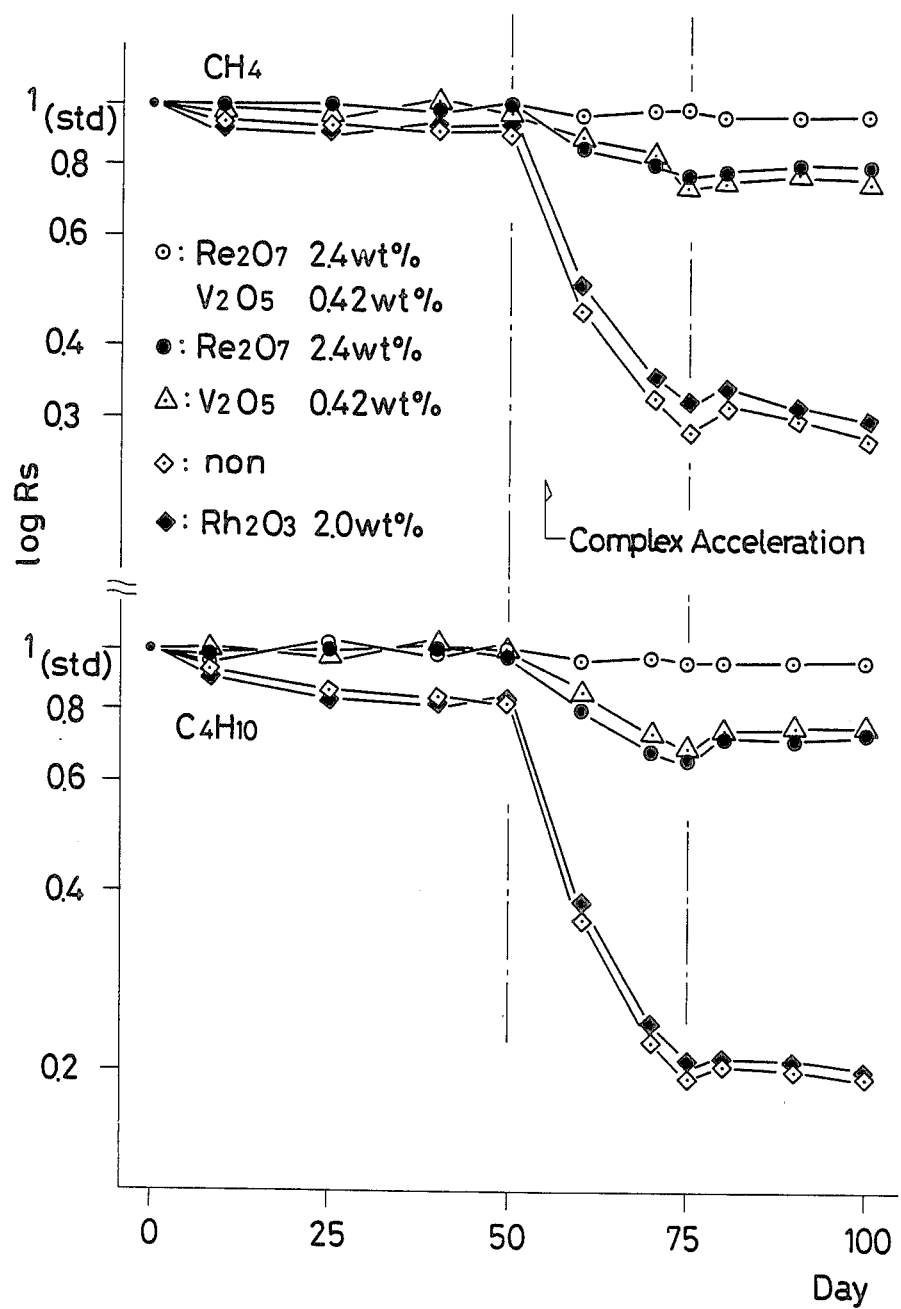
FIG. 7 shows the characteristics of a sensor with respect to complex acceleration.

A complex acceleration test is carried out according to the Japanese inspecting standard for gas leak alarms for town gas. In this test the heater voltage and the detection voltage are increased by 10% respectively and the sensor is used for no less than one month in an atmosphere of 1000 ppm of hydrogen at 50° C. and 40% relative humidity. That is, an atmosphere of high temperature and humidity and the influence due to gas are applied simultaneously to the sensor. It can be said that this test is very severe particularly for a self-heating sensor. Since the resistance of the sensor is lowered in gases, the sensor itself generates heat and its temperature rises considerably. FIG. 7 and Table 10 show the results of such complex acceleration tests. Composition of the samples and the expression of the measured values are the same in FIG. 6 and Table 9.

TABLE 10

(Complex acceleration)
Ratio between resistance values (before/after test)

| Sample No. | Additive | (wt %) | $C_4H_{10}$ | $CH_4$ |
|---|---|---|---|---|
| 1 | — | | 0.25 | 0.3 |
| 2 | $Re_2O_7$ | 2.4 | 0.7 | 0.8 |
| 7 | $Re_2O_7$ | 2.4 | 1.0 | 1.0 |
|  | $V_2O_5$ | 0.12 | | |
| 3 | $Re_2O_7$ | 2.4 | 1.0 | 1.0 |
|  | $V_2O_5$ | 0.42 | | |

TABLE 10-continued (Complex acceleration)
Ratio between resistance values (before/after test)

| Sample No. | Additive | (wt %) | $C_4H_{10}$ | $CH_4$ |
|---|---|---|---|---|
| 8 | $Re_2O_7$ | 2.4 | 1.0 | 1.0 |
|  | $V_2O_5$ | 0.9 | | |
| 9 | $Re_2O_7$ | 0.64 | 1.0 | 1.0 |
|  | $V_2O_5$ | 0.9 | | |
| 1s* | — | | 0.6 | 0.8 |
| 3s | $Re_2O_7$ | 2.4 | 1.0 | 1.0 |
|  | $V_2O_5$ | 0.42 | | |

*The result obtained under the service condition of heating at constant temperature.

The influences of the complex acceleration can be reduced by addition of rhenium alone, but a more preferable effect is obtained when using rhenium and vanadium together. Sufficient durability against the complex acceleration is obtained in the range of 0.1 to 15 wt. % of rhenium and 0.05 to 1.5 wt. % of vanadium, and more preferably in the range of 0.4 to 8 wt. % of rhenium. and 0.05 to 1.5 wt. % of vanadium.

Figure 8:
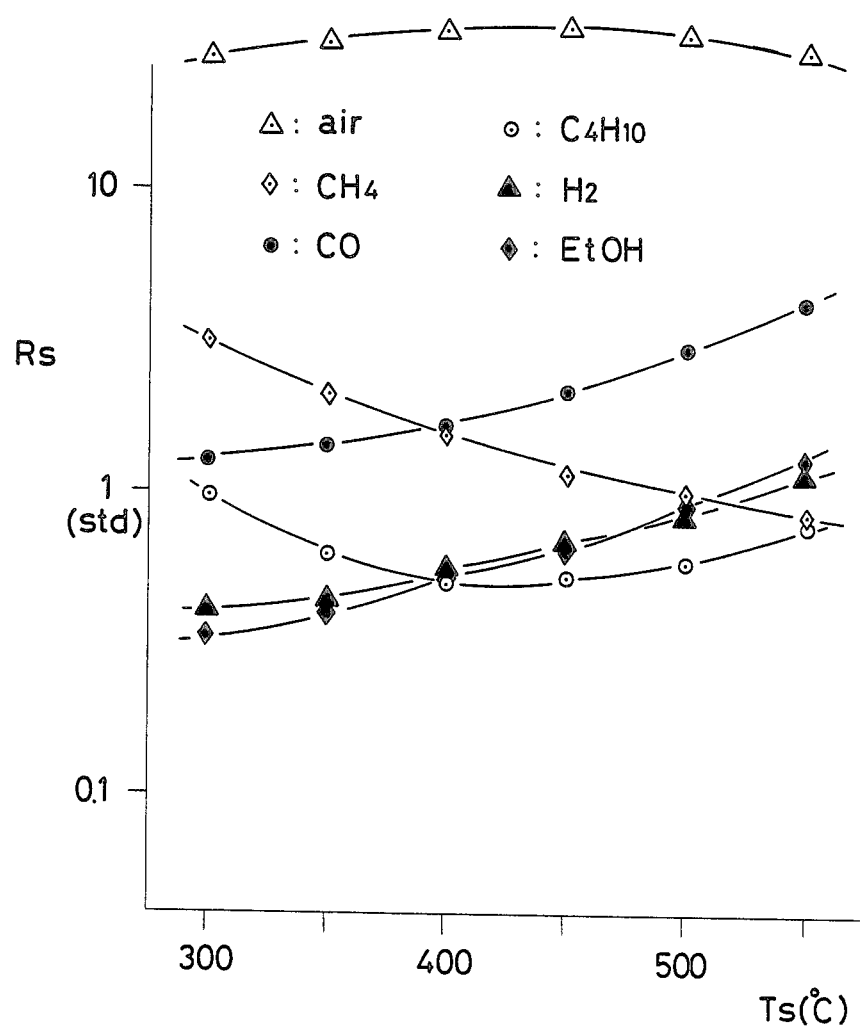
FIGS. 8 and 9 show the characteristics of gas sensors of the embodiments with respect to heating temperature.
Figure 9:
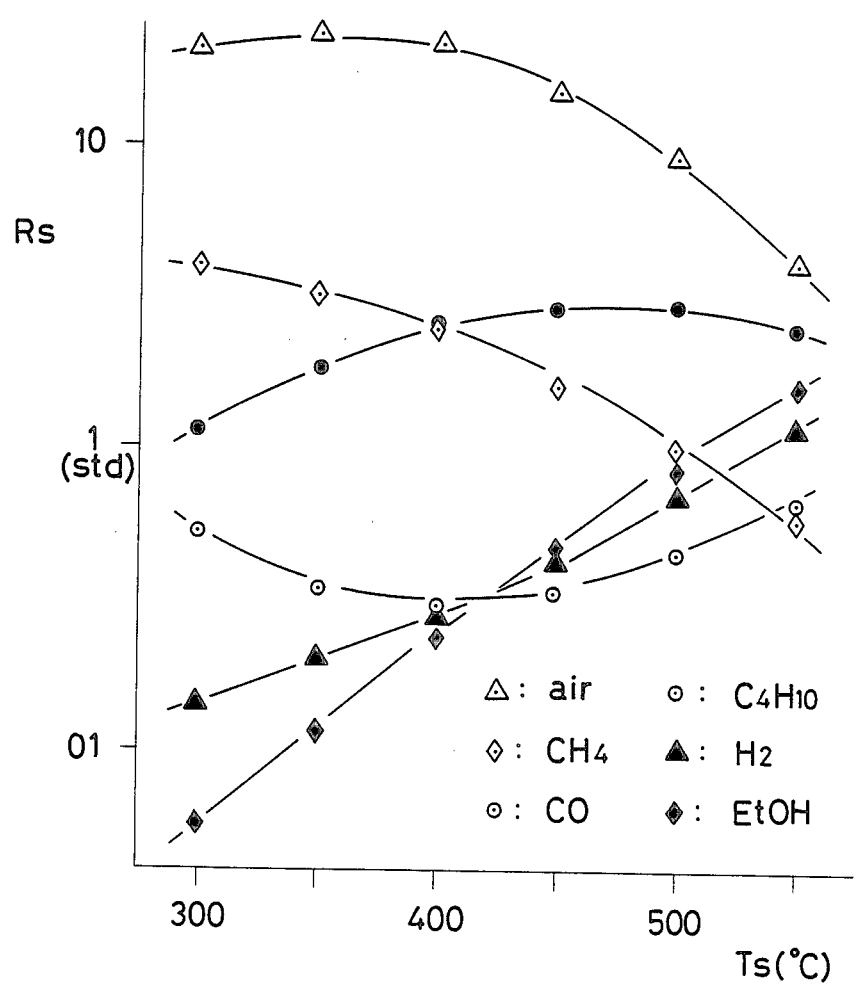

FIGS. 8 and 9 show the sensor dependence on the heating temperature when 2.4 wt. % of $Re_2O_7$ and 0.42 wt. % of $V_2O_5$ are added. That is, FIG. 8 shows a result when rhenium, etc. is segregated on the surface, while FIG. 9 shows a result when rhenium is uniformly added to $SnO_2$. In both figures the values are shown establishing each resistance value in 3500 ppm of methane at 550° C. as a reference. The sensor is uniformly heated by means of two heaters (6), (8).

The sensors dependence on heating temperature increases gently when rhenium is impregnated on the surface, while it increases sharply when rhenium is uniformly added. Accordingly, when employing rhenium on the surface only, the detection error due to the fluctuation of the heating temperature is reduced. Also this effect is almost the same when rhenium is added alone and when the amount of rhenium and vanadium additions are changed.

For uniform addition of rhenium, the resistance value in air at high temperature is low, which means that there is the possibility of the occurrence of the so-called breakdown, which is a phenomenon in which the output is not lowered despite the lowering of gas density after a self-heating sensor contacts a gas of high density. This breakdown does not always occur on contact with gases of high density, but rather occurs at random due to the increase in the supply voltage.

In evaluating breakdowns, 100 units of sensors are used under self-heating service conditions by increasing the heater voltage and the supply voltage by 10% respectively. Each sensor is exposed to 5000 ppm of isobutane for five minutes, and then the gas is freed. If the resistance value of a sensor after five minutes from releasing the gas is lower than a resistance value of 1000 ppm of isobutane, then a breakdown is said to occur. Table 11 shows results of the evaluation.

TABLE 11

(Breakdown)

| Sample No. | Additive | (wt %) | Frequency of breakdown (%) |
|---|---|---|---|
| 2 | $Re_2O_7$ | 2.4 impregnated | 0 |
| 3 | $Re_2O_7$ | 2.4 | 0 |
|  | $V_2O_5$ | 0.42 impregnated | |
| 32 | $Re_2O_7$ | 2.4 uniformly added | 5 |
| 33 | $Re_2O_7$ | 2.4 | |
|  | $V_2O_5$ | 0.42 uniformly added | 7 |

Modification

Figure 10:
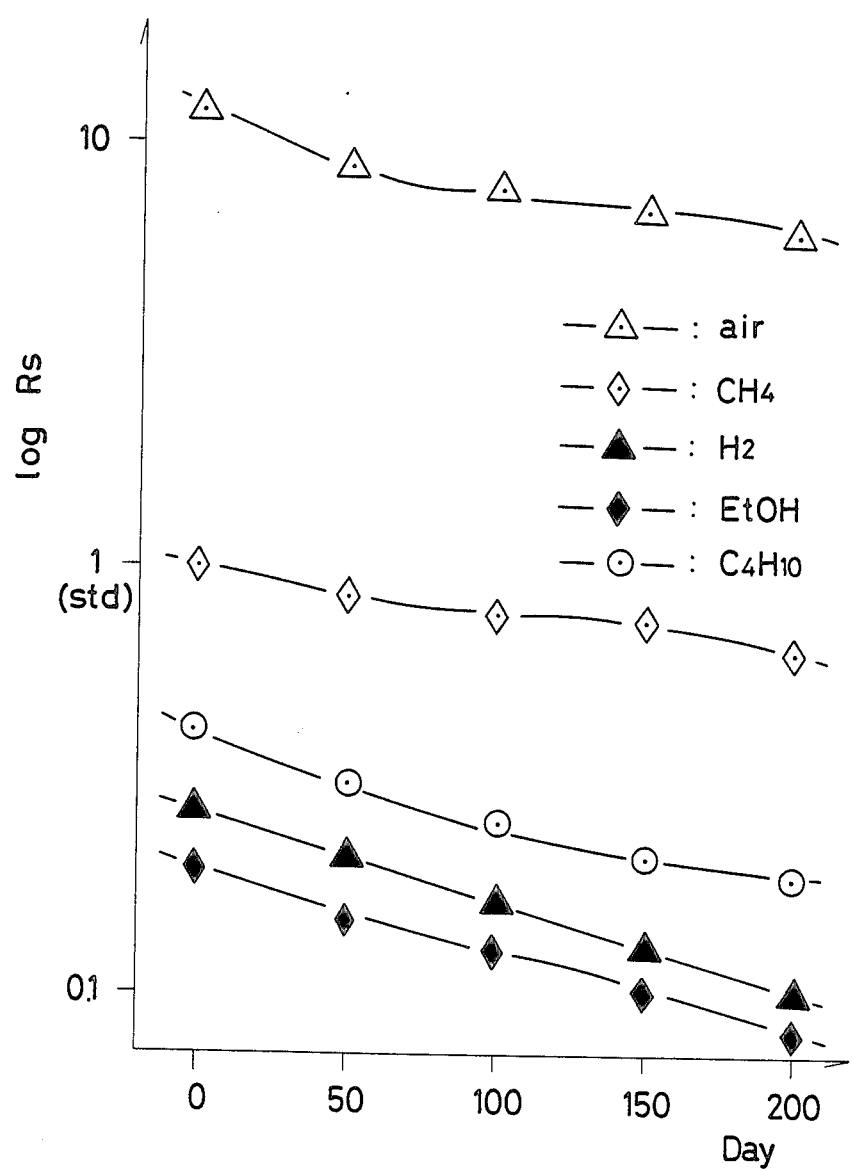
FIG. 10 shows the characteristics of a prior art gas sensor over 220 days.
Figure 11:
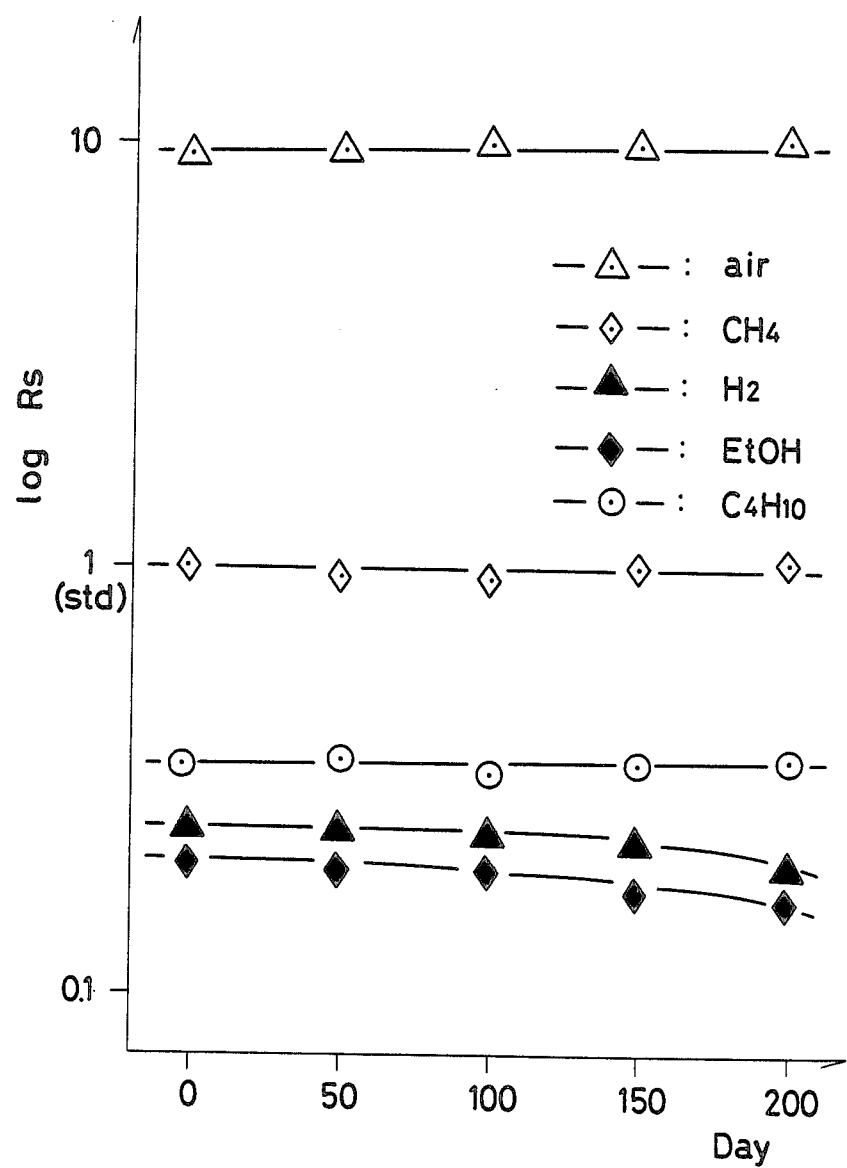
FIG. 11 shows the characteristics of gas sensors of the embodiment over 220 days.

Described below are the results of tests for various modifications. The conditions for the preparation of these sensors are the same as for the previous examples. In addition, a test is carried out on samples in which the baking temperature of SnO₂ is 700° C., and almost the same result is obtained. The self-heating circuit shown in FIG. 4 is used for measurement, and the same measuring method is used as described above. But, since they are different from the foregoing examples, the four sensors are tested, and circuit conditions are changed. Further, the temperature of each sensor is set to 350° C. in clean air while 450° to 500° C. in gases, and the density of gases is set to 1000 ppm. FIGS. 10 and 11 show transitory characteristics of a sensor in which 0.4 wt. % of PdO is added to SnO₂ and a binder of 3 wt. % of ethyl silicate is used. FIG. 10 shows a comparative example without addition of rhenium, while FIG. 11 shows an example in which 2 wt. % of rhenium is uniformly added to SnO₂.

Tables 12 to 14 show other results. Effect of the addition is shown in the form of an inhibition rate of lowering of resistance. The inhibition rate is expressed by:

$$1 - \Delta Rs/Rs.Rref / \Delta Rref$$

where:
- Rs is an initial resistance value of a rhenium added sensor.
- ΔRs is the change in resistance of a sensor containing rhenium.
- Rref is an initial resistance value of a sensor that does not contain rhenium, and
- ΔRref is the change in of resistance of a sensor without rhenium.

There are no differences between the sensors except for the addition of rhenium.

Table 12 shows results when rhenium is uniformly added to SnO₂. In addition, silica is added in the form of ethyl silicate, and PdO is added at the same time as the rhenium. In the comparative example, vanadium is uniformly added to SnO₂. Additives other than rhenium are also shown as basic materials. From Table 12 it is found that the effect of rhenium is large when silica is added together (samples 7, 8), and that a complex action takes place between rhenium and paradium (samples 2, 7 and 5, 8). It is noted that sample 9, in which 0.8 wt % of V₂O is added (without rhenium), exhibits an effect equal to sample 2 in which 2.0 wt. % of rhenium is added. However, with respect to durability against overheating, vanadium is inferior to rhenium.

From Table 13, it is found that rhenium is also effective when combined with noble metals such as pt, Ir, etc. In this connection, rhenium and Pt, etc. are uniformly added to SnO₂, and silica is added in the form of ethyl silicate.

From Table 14, it is found that effect of rhenium is sufficiently exhibited irrespective of whether its added by impregnation to form a layer on the surface or added to the aggregate. Furthermore, a high effect is also achieved when combining rhenium with a catalyst of a transition metal oxide such as Mn₂O₃ or Fe₂O₃.

The materials which are effective for the inhibition of lowering of resistance are vanadium and rhenium. The change (lowering) of resistance with time cannot be inhibited by adding 5 wt. % of TiO₂, Cr₂O₃, Fe₂O₃, NiO, CuO, ZnO, ZrO₂, MO₃, WO₃, or Ta₂O (each containing 3 wt. % of SiO₂) by impregnation instead of rhenium. The change (lowering) of resistance cannot be inhibited, either, by addition of noble metals such as PdO, Pt, Ir, Os, RuO₂, Au, etc., unless they are used in conjunction with rhenium.

The invention is not limited to these examples described above, and it is further possible to change heating conditions or to add various additives as is done in the known art.

TABLE 12

(Rhenium and silica, paradium)

| Sample No. | Basic Material | (wt %) | Re₂O₇ (wt %) | Effect in inhibition rate (%) | | | | | |
|---|---|---|---|---|---|---|---|---|---|
| | | | | H₂ | EtOH | CH₄ | Air | C₄H₁₀ | CO |
| 1 | SiO₂ PdO | 3+ 0.4 | 0.5 | 70 | 60 | 100 | 100 | 100 | 100 |
| 2 (a) | | " | 2.0 | 85 | 80 | 100 | 100 | 100 | 100 |
| 3 | | " | 6.0 | 90 | 90 | 100 | 100 | 100 | 100 |
| 4 | PdO | 0.4 | 0.3 | 40 | 30 | 80 | 90 | | |
| 5 | | " | 2.0 | 65 | 60 | 90 | 100 | | |
| 6 | | " | 10 | 80 | 70 | 100 | 100 | | |
| 7 | SiO₂ | 3 | 2.0 | 70 | 65 | 95 | 100 | | |
| 8 | — | | 2.0 | 40 | 30 | 90 | 80 | | |
| 9 (b) | SiO₂ PdO | 3+ 0.4 + V₂O₅ | — 0.8 | 80 | 85 | 100 | 100 | | | where:
(a) is the sample shown in FIG. 11, and
(b) is a comparative example.

TABLE 13

(In Combination with a catalyst)

| Sample No. | Basic Material | (wt %) | Re₂O₇ (wt %) | Effect in inhibition rate (%) | | | |
|---|---|---|---|---|---|---|---|
| | | | | H₂ | EtOH | CH₄ | Air |
| 1 | SiO₂ Pt | 3+ 0.3 | 2.0 | 80 | 80 | 100 | 100 |
| 2 | Pt | 0.3 | 2.0 | 60 | 60 | 90 | 100 |
| 3 | SiO₂ Ir | 3+ 0.2 | 2.0 | 80 | 75 | 100 | 100 |

TABLE 14

(Addition by impregnation or to an aggregate)

| Sample No. | Basic Material | (wt %) | Re₂O₇ (wt %) | Effect in inhibition rate (%) | | | |
|---|---|---|---|---|---|---|---|
| | | | | H₂ | EtOH | CH₄ | Air |
| 1 | SiO₂ PdO | 3+ 0.4 | 2.0 | 90 | 85 | 100 | 100 |
| | Rhenium and PdO are added by impregnation | | | | | | |
| 2 | SiO₃ Mn₂O₃ | 3+ 0.5 | 3.0 | 80 | 75 | 100 | 100 |
| | Rhenium and Mn are added by impregnation | | | | | | |
| 3 | SiO₂ Fe₂O₃ | 3+ 0.3 | 3.0 | 80 | 80 | 100 | 100 |
| | Rhenium and Fe are added by impregnation | | | | | | |
| 4* | SiO₂ | 3+ | 3.0 | 80 | 80 | 100 | 100 |

TABLE 14-continued

| Sample No. | Basic Material (wt %) | Re$_2$O$_7$ (wt %) | Effect in inhibition rate (%) | | | |
|---|---|---|---|---|---|---|
| | | | H$_2$ | EtOH | CH$_4$ | Air |
| | PdO | 0.5 | | | | |

(Addition by impregnation or to an aggregate)

*alumina carrying rhenium or paradium is mixed with SnO$_2$ in equal weight to form a sensitive element (4).

What is claimed is:

1. A gas sensor which comprises:
an electrode; and
a gas sensitive element which is connected to said electrode, said gas sensitive element comprising:
SnO$_2$; and
at least one rhenium containing material selected from the group consisting of elemental rhenium and oxides of rhenium.

2. A gas sensor of claim 1 wherein said rhenium containing material is substantially uniformly dispersed throughout said gas sensitive element and said rhenium containing material is present in a weight ratio of about 1 to about 150 mg of said rhenium containing material per gram of SnO$_2$.

3. A gas sensor of claim 1 wherein said rhenium containing material is substantially uniformly dispersed on the surface of said gas sensitive element.

4. A gas sensor of claims 1 or 3 wherein said gas sensitive element further comprises:
vanadium oxide.

5. A gas sensor of claim 1 wherein said rhenium containing material is substantially uniformly dispersed within a thermal resistant insulating material which is incorrporated into the gas sensitive element.

6. A gas sensor of claim 5 wherein said gas sensitive element further comprises silica.

* * * * *